United States Patent [19]

Cooper et al.

[11] Patent Number: 5,296,363
[45] Date of Patent: Mar. 22, 1994

[54] PREPARATION OF 2-(4-HYDROXYPHENOXY)PROPIONIC ACID BY FERMENTATION

[75] Inventors: Bryan Cooper, Mannheim; Wolgang Ladner; Bernhard Hauer, both of Fussgoenheim; Hardo Siegel, Speyer, all of Fed. Rep. of Germany

[73] Assignee: Base Aktiengesellschaft, Ludwigshafen, Fed. Rep. of Germany

[21] Appl. No.: 761,343

[22] PCT Filed: Mar. 22, 1990

[86] PCT No.: PCT/EP90/00472
§ 371 Date: Sep. 10, 1991
§ 102(e) Date: Sep. 10, 1991

[87] PCT Pub. No.: WO90/11362
PCT Pub. Date: Oct. 4, 1990

[30] Foreign Application Priority Data

Mar. 28, 1989 [DE] Fed. Rep. of Germany ....... 3910024

[51] Int. Cl.$^5$ ............ C12P 7/42; C12P 7/52; C12P 7/40
[52] U.S. Cl. ............................... 435/146; 435/135; 435/136
[58] Field of Search ................ 435/146, 135, 136

[56] References Cited

U.S. PATENT DOCUMENTS

| | | |
|---|---|---|
| 4,565,782 | 1/1986 | Bewick ............... 435/146 |
| 4,568,641 | 2/1986 | Bewick ............... 435/135 |
| 5,037,759 | 8/1991 | Clifford et al. ....... 435/136 |
| 5,075,233 | 12/1991 | Bertola et al. ........ 435/136 |
| 5,089,405 | 2/1992 | Cerbelaud et al. .... 435/136 |

OTHER PUBLICATIONS

*Fungal Detoxication*, Byrde et al., Biochemical Journal 65 (1975) pp. 682–686.

*Primary Examiner*—Herbert J. Lilling
*Attorney, Agent, or Firm*—Keil & Weinkauf

[57] ABSTRACT

A process for the oxidation of 2-phenoxypropionic acid to 2-(4-hydrophenoxy)propionic acid using microorganisms is described.

5 Claims, No Drawings

PREPARATION OF 2-(4-HYDROXYPHENOXY)PROPIONIC ACID BY FERMENTATION

The present invention relates to a process for the preparation of 2-(4-hydroxyphenoxy)propionic acid.

2-(4-Hydroxyphenoxy)propionic acid is a valuable intermediate, in particular for the preparation of herbicides.

Chemical processes for the preparation of racemic and of pure enantiomeric forms of 2-(4-hydroxyphenoxy)propionic acid have been disclosed. These processes start from hydroquinone and have the disadvantage that they give by-products whose removal, which is necessary, is laborious. This makes economic preparation impossible.

It has been disclosed that microorganisms are able to hydroxylate aromatic compounds. This usually produces dihydroxylated compounds or mixtures of various regioisomers (R. J. W. Byrde, D. Woodcook, Biochem. J. 65 (1957) 682).

The regioselective oxidation of 2-phenoxypropionic acid to 2-(4-hydroxyphenoxy)propionic acid by microorganisms has not hitherto been disclosed.

We have now found, surprisingly, that various microorganisms oxidize the valuable 2-phenoxypropionic acid to 2-(4-hydroxyphenoxy)propionic acid with high regioselectivity.

The present invention relates to a process for the preparation of 2-(4-hydroxyphenoxy)propionic acid by fermentation, which comprises oxidizing 2-phenoxypropionic acid or salts thereof under aerobic conditions in the presence of a microorganism.

A large number of microorganisms are suitable for the process, in particular fungi and bacteria. Utilizable fungi can be isolated, for example, from soil samples, in particular humus-containing soil samples. Particularly suitable for the reaction are *Aspergillus niger* strains. Also suitable are many fungi from the genera Beauveria, Paecilomyces, Sclerotium and Coprinus, which can be obtained, for example, from collections of strains and whose suitability for the hydroxylation can be determined in a straightforward preliminary test. Suitable bacteria can also be isolated from soil samples, inter alia. Particularly suitable bacteria are Streptomyces strains.

To carry out the process according to the invention, suitable strains are transferred to a nutrient medium containing 2-phenoxypropionic acid and incubated aerobically therein under conditions favorable for growth and production by the particular microorganism. The fermentation is carried out continuously or batchwise for 1 to 10 days.

The cells of the microorganism, which can also be used in the form of dormant, non-growing cells, are allowed to act directly on the substrate. All conventional incubation processes can be employed, but particularly preferred fermenters are in the form of deep, aerated and agitated tanks. Very good results are obtained by incubation of a liquid nutrient medium.

Suitable nutrient media contain sources of carbon and of nitrogen, and inorganic salts and, where appropriate, small amounts of trace elements and vitamins. Sources of nitrogen which can be used are inorganic or organic nitrogen compounds or materials which contain these compounds. Examples are ammonium salts, nitrates, corn steep liquor, brewer's yeast autolysate, soybean meal, wheat gluten, yeast extract, yeast, urea and potato protein. Examples of sources of carbon which can be used are sugars such as glucose, polyols such as glycerol, or fats such as soybean oil.

Examples of inorganic salts are the salts of calcium, magnesium, manganese, potassium, zinc, copper, iron and other metals. A particularly suitable anion in the salts is the phosphate ion. Growth factors may be added to the nutrient medium, such as biotin, riboflavin or other vitamins.

The ratios of the said nutrients in the mixture depends on the type of fermentation and will be determined in the individual case.

Generally suitable for carrying out the process according to the invention are phenoxypropionic acid concentrations of about 1 to 100 g/l, preferably about 5 to 50 g/l.

The culture conditions are chosen so that the best possible yields are achieved. Cultivation is preferably carried out at from 20° to 40° C., particularly advantageously from 25° to 30° C. The pH is preferably maintained in the range 3 to 9. The pH is particularly advantageously from 4 to 7. An incubation time of from 15 to 100 hours generally suffices. The maximum amount of the desired product accumulates in the medium during this time. The acid is preferably added in the form of a salt, e.g. the sodium salt. The acid can be added to the nutrient medium all at once at the start, after growth has taken place or in several portions or continuously during the cultivation.

The use of 2-phenoxypropionic acid is preferred, but it is also possible to use salts thereof. Preferred salts are alkali metal and alkaline earth metal salts, for example the Na, K and Li salts.

The novel process is suitable for the oxidation both of racemic 2-(4-hydroxyphenoxy)propionic acid and of antipodes thereof. The center of asymmetry remains untouched in the process according to the invention. If, for example, R-2-phenoxypropionic acid is used, the configuration is retained and the product is R-2-(4-hydroxyphenoxy)propionic acid. No other hydroxylation products are found in the reaction. Thus the novel process represents a straightforward and more economic method for the selective preparation of 2-(4-hydroxyphenoxy)propionic acid.

The examples which follow illustrate the invention:

EXAMPLE 1

Two liquid nutrient media were used to examine various strains of bacteria:

| Medium A | |
|---|---|
| 20 g/l | glucose |
| 5 g/l | yeast extract |
| 5 g/l | ammonium sulfate |
| 0.5 g/l | magnesium sulfate 7-hydrate |
| 0.05 g/l | manganese sulfate 1-hydrate |
| 1.5 g/l | potassium dihydrogen phosphate |
| 3.6 g/l | dipotassium hydrogen phosphate |
| 1 g/l | (R)-2-phenoxypropionic acid |
| 2 mg/l | iron(II) sulfate 1-hydrate |
| 100 µg/l | zinc(II) sulfate 4-hydrate |
| 300 µg/l | boric acid |
| 200 µg/l | cobalt(II) chloride 6-hydrate |
| 10 µg/l | copper(II) chloride 2-hydrate |
| 20 µg/l | nickel(II) chloride 6-hydrate |
| 30 µg/l | sodium molybdate 2-hydrate |

The pH was adjusted to 6.8 with 5N sodium hydroxide solution. Glucose and phosphates were each autoclaved separately at 121° C. for 10 minutes. The (R)-2-phenoxypropionic acid was dissolved in water, with a little 5N sodium hydroxide solution, and sterilized by filtration. The remaining medium was autoclaved at 121° C. for 10 minutes.

| Medium B | | |
|---|---|---|
| 20 g/l | glucose | |
| 40 g/l | corn steep liquor | |
| 1.5 g/l | potassium dihydrogen phosphate | |
| 3.6 g/l | dipotassium hydrogen phosphate | |
| 1 g/l | (R)-2-phenoxypropionic acid | |

The pH was adjusted to 6.8 with 5N sodium hydroxide solution. Glucose and phosphates were each autoclaved separately at 121° C. for 10 minutes. The (R)-2-phenoxypropionic acid was dissolved in water, with a little 5N sodium hydroxide solution, and sterilized by filtration. The remaining medium was autoclaved at 121° C. for 45 minutes.

20 ml portions of the sterile medium were introduced into sterile 100 ml Erlenmeyer flasks, which were provided with a sterile cotton plug. One loop of the strain of bacteria to be tested was used to inoculate each flask. The flasks were then incubated at 28° C., shaking at 250 rpm, for 3 to 7 days. Then 1000 μl of fermentation broth were removed, 100 μl of 1N HCl and 800 μl of ethyl acetate were added, and the mixture was vigorously mixed for 15 seconds. 700 μl of the organic phase were carefully removed and evaporated in a test tube under a gentle stream of nitrogen at 50° C. The residue was dissolved in 70 μl of ethyl acetate and transferred quantitatively into a test tube for the gas chromatography. To this were added 30 μl of N-methyl-N-trimethylsilyl-trifluoroacetamide (MSTFA). The samples were then examined by gas chromatography. The external standard used was an authentic sample of (R,S)-2-(4-hydroxyphenoxy)propionic acid which had been chemically synthesized.

The table which follows summarizes the results:

| Genus/species | Collection/ Number | Conversion (%) | Medium |
|---|---|---|---|
| Streptomyces antibioticus | DSM 40725 | 11 | A |
| Streptomyces antibioticus | ATCC 11891 | 10 | A |
| Streptomyces flocculus | ATCC 13850 | 18 | A |
| Streptomyces hygroscopicus | ATCC 19040 | 97 | B |
| Streptomyces hygroscopicus | ATCC 21705 | 98 | A |
| Streptomyces kasugaensis | ATCC 15715 | 4 | A |
| Streptomyces kasugaensis | ATCC 15714 | 23 | B |
| Streptomyces mediocidicus | ATCC 13279 | 13 | A |
| Streptomyces niveus | ATCC 19793 | 23 | A |
| Streptomyces panayensis | ATCC 31055 | 2 | A |
| Streptomyces roseochromogenes | ATCC 21895 | 4 | A |
| Streptomyces viridifaciens | ATCC 11989 | 24 | A |

EXAMPLE 2

About 400 different novel Streptomycetes strains were isolated from various soil samples by the method of DREWS (Mikrobiologisches Praktikum, 3rd edition, Springer Verlag, pages 47–48, 1976). These strains were tested by the method of Example 1. The table which follows summarizes the conversion by the strains identified as positive.

| Strain number | Conversion (%) | Medium |
|---|---|---|
| 1034 | 8 | A |
| 1045 | 28 | A |
| 1053 | 22 | A |
| 1057 | 7 | A |
| 1071 | 11 | A |
| 2476 | 13 | A |
| 3279 | 4 | A |
| 3292 | 33 | B |
| 3388 | 26 | B |
| 3520 | 42 | B |
| 3523 | 80 | A |
| 3549 | 80 | B |
| 3558 | 24 | A |
| 3559 | 32 | A |
| 3560 | 98 | A |
| 3561 | 90 | A |
| 3565 | 4 | A |
| 3567 | 72 | B |
| 3574 | 41 | A |
| 3575 | 24 | B |
| 3782 | 44 | A |
| 3925 | 24 | B |
| 4041 | 14 | A |
| 5431 | 19 | A |
| 5432 | 99 | A |
| 5607 | 24 | A |
| 5608 | 26 | A |
| 5613 | 33 | A |
| 5619 | 51 | A |
| 5632 | 18 | A |
| 5635 | 15 | A |
| 5636 | 5 | A |
| 5637 | 39 | A |
| 5638 | 38 | A |
| 5648 | 25 | A |
| 5654 | 59 | A |

EXAMPLE 3

A liquid nutrient medium was prepared with the following ingredients:

| | |
|---|---|
| 20 g/l | glucose |
| 5 g/l | yeast extract |
| 5 g/l | ammonium sulfate |
| 0.5 g/l | magnesium sulfate 7-hydrate |
| 0.05 g/l | manganese sulfate 1-hydrate |
| 1.5 g/l | potassium dihydrogen phosphate |
| 3.6 g/l | dipotassium hydrogen phosphate |
| 3 g/l | Carbopol ® 946 (Carboxyvinyl polymer with an extremely high molecular weight) |
| 3 g/l | (R)-2-phenoxypropionic acid |
| 2 mg/l | iron(II) sulfate 1-hydrate |
| 100 μg/l | zinc(II) sulfate 4-hydrate |
| 300 μg/l | boric acid |
| 200 μg/l | cobalt(II) chloride 6-hydrate |
| 10 μg/l | copper(II) chloride 2-hydrate |
| 20 μg/l | nickel(II) chloride 6-hydrate |
| 30 μg/l | sodium molybdate 2-hydrate |

The pH was adjusted to 6.8 with 5N sodium hydroxide solution. Glucose and phosphates were each autoclaved separately at 121° C. for 10 minutes. The (R)-2-phenoxypropionic acid was dissolved in water with a little 5N sodium hydroxide solution and sterilized by filtration. The remaining medium was autoclaved at 121° C. for 10 minutes. 20 ml portions of the sterile medium were introduced into sterile 100 ml Erlenmeyer flasks, which were provided with a sterile cotton plug. One loop of spores of the *Aspergillus niger* ATCC 11394 fungus strain was used to inoculate one flask. The flask was then incubated at 28° C., shaking at 250 rpm, for three days. Then 1000 μl of fermentation broth were removed, 100 μl of 1N HCl and 800 μl of ethyl acetate were added, and the mixture was vigorously mixed for 15 seconds. 700 μl of the organic phase were carefully removed and evaporated in a test tube under a gentle stream of nitrogen at 50° C. The residue was dissolved in 70 μl of ethyl acetate and transferred quantitatively into a test tube for the gas chromatography. To this were added 30 μl of N-methyl-N-trimethylsilyltrifluoroacetamide (MSTFA). The sample was then examined by gas chromatography. An authentic sample of 2-)(4-hydroxyphenoxy)-propionic acid was sued as reference.

EXAMPLE 4

A liquid nutrient medium was prepared with the following ingredients:

| | |
|---|---|
| 40 g/l | glucose |
| 10 g/l | yeast extract |
| 0.5 g/l | magnesium sulfate 7-hydrate |
| 0.05 g/l | manganese sulfate 1-hydrate |
| 1.5 g/l | potassium dihydrogen phosphate |
| 3.6 g/l | dipotassium hydrogen phosphate |
| 20 g/l | (R)-2-phenoxypropionic acid |
| 2 mg/l | iron(II) sulfate 1-hydrate |
| 100 μg/l | zinc(II) sulfate 4-hydrate |
| 300 μg/l | boric acid |
| 200 μg/l | cobalt(II) chloride 6-hydrate |
| 10 μg/l | copper(II) chloride 2-hydrate |
| 20 μg/l | nickel(II) chloride 6-hydrate |
| 30 μg/l | sodium molybdate 2-hydrate |

The pH was adjusted to 6.8 with 5N sodium hydroxide solution. Glucose and phosphates were each autoclaved separately at 121° C. for 10 minutes. The (R)-2-phenoxypropionic acid was dissolved in water with a little 5N sodium hydroxide solution and sterilized by filtration. The remaining medium was autoclaved at 121° C. for 10 minutes. 50 ml of the sterile medium were introduced into a sterile 100 ml Erlenmeyer flask, which was provided with a sterile cotton plug.

After inoculation wit 2.5 ml of a 72 h-old preculture of *Beauveria bassiana* ATCC 7159 (cultured in the same medium but in the presence of only 5g/l (η)-2-phenoxypropionic acid), the mixture was incubated at 28° C., shaking at 200 rpm, for 4–5 days. The subsequent analysis by gas chromatography revealed that the acid had been 98% hydroxylated.

98% of the (R)-2-phenoxypropionic acid had been oxidized to (R)-2-(4-hydroxyphenoxy)propionic acid. The result was the same when the S enantiomer or the racemate of 2-phenoxypropionic acid was employed.

EXAMPLE 5

A novel strain of *Aspergillus niger* was isolated from a humus-containing soil sample by the method of DREWS (Mikrobiologisches Praktikum, 3rd edition, Springer Verlag, pages 51–53 (1976)). This strain (No. 1777) was tested by the method of Example 3. 99.8% of the acid had been oxidized after 3 days.

EXAMPLE 6

Further strains of the species *Aspergillus niger* were tested as described in Example 3 and analyzed after fermentation for 3 and 7 days. The results are summarized in the table which follows:

| Genus/species | Collection/Number | Conversion (%) | Days |
|---|---|---|---|
| *Aspergillus niger* | ATCC 9142 | 34 | 3 |
| | ATCC 11394 | 98 | 3 |
| *Aspergillus niger* | ATCC 26693 | 100 | 3 |
| *Aspergillus niger* | ATCC 1015 | 83 | 3 |
| *Aspergillus niger* | ATCC 10577 | 70 | 3 |
| *Aspergillus niger* | ATCC 13794 | 99 | 3 |
| *Aspergillus niger* | ATCC 11414 | 79 | 3 |
| *Aspergillus niger* | ATCC 26550 | 79 | 3 |
| *Aspergillus niger* | ATCC 9029 | 71 | 3 |
| *Aspergillus niger* | ATCC 9642 | 41 | 3 |
| *Aspergillus niger* | ATCC 32656 | 27 | 7 |
| *Aspergillus niger* | ATCC 6275 | 11 | 3 |
| *Aspergillus niger* | ATCC 16404 | 97 | 3 |
| *Aspergillus niger* | ATCC 10575 | 53 | 7 |
| *Aspergillus niger* | ATCC 10581 | 85 | 3 |
| *Aspergillus niger* | ATCC 10549 | 27 | 7 |
| *Aspergillus niger* | ATCC 1027 | 51 | 7 |
| *Aspergillus niger* | ATCC 1040 | 97 | 7 |
| *Aspergillus niger* | ATCC 10553 | 14 | 7 |
| *Aspergillus niger* | ATCC 10864 | 65 | 7 |
| *Aspergillus niger* | ATCC 1004 | 79 | 7 |
| *Aspergillus niger* | ATCC 16880 | 99 | 7 |
| *Aspergillus niger* | ATCC 16888 | 54 | 7 |
| *Aspergillus niger* | ATCC 6273 | 89 | 7 |
| *Aspergillus niger* | ATCC 7797 | 79 | 7 |
| *Aspergillus niger* | ATCC 7983 | 90 | 7 |
| *Aspergillus niger* | ATCC 10574 | 100 | 7 |
| *Aspergillus niger* | ATCC 10578 | 100 | 7 |

EXAMPLE 7

Further fungi were tested as in Example 3 and analyzed after fermentation for 3 and 7 days.

| Genus/species | Collection/Number | Conversion (%) | Days |
|---|---|---|---|
| *Aspergillus carbonarius* | ATCC 8740 | 7 | 7 |
| *Aspergillus carbonarius* | ATCC 6276 | 5 | 7 |
| *Aspergillus foetidus* | ATCC 10254 | 62 | 7 |
| *Aspergillus parasiticus* | ATCC 26850 | 7 | 3 |
| *Aspergillus sclerotiorum* | DSM 63357 | 5 | 3 |
| *Aspergillus sclerotiorum* | CMI 112328 | 17 | 3 |
| *Aspergillus sclerotiorum* | CMI 116935 | 15 | 3 |
| *Beauveria bassiana* | ATCC 7159 | 99 | 3 |
| *Paecilomyces farinosus* | ATCC 26853 | 63 | 7 |
| *Sclerotium rolfsii* | ATCC 15206 | 85 | 7 |
| *Sclerotium rolfsii* | ATCC 15204 | 19 | 7 |
| *Sclerotium rolfsii* | ATCC 15203 | 89 | 7 |
| *Sclerotium rolfsii* | ATCC 15201 | 81 | 7 |
| *Sclerotium rolfsii* | ATCC 15195 | 85 | 7 |
| *Sclerotium rolfsii* | ATCC 26326 | 4 | 7 |
| *Sclerotium delphinii* | ATCC 15196 | 1 | 7 |
| *Coprinus cinereus* | ATCC 20120 | 2 | 7 |

We claim:

1. A process for the preparation of 2-(4-hydroxyphenoxy)propionic acid by fermentation, wherein hydroxylation takes place substantially only in the p-position, which process comprises oxidizing 2-phenoxypropionic acid of salts thereof under aerobic conditions in the presence of a 2-(4-hydroxyphenoxy) propionic acid activity-producing, soil-inhabiting microorganism selected from the group consisting of a Streptomycetes bacteria and a fungus.

2. The process of claim 1 wherein the microorganism is an *Aspergillus niger* fungus.

3. The process of claim 1 wherein the microorganism is a Streptomycetes bacterium.

4. A process as defined in claim 1 wherein the enantiomers of 2-phenoxypropionic acid are employed.

5. The process of claim 1, wherein the microorganism is a fungus selected from the group consisting of *Beauveria bassiana, Paecilomyces farinosus, Sclerotium folfsii, Sclerotium delphinii,* and *Coprinus cinereus.*

* * * * *

UNITED STATES PATENT AND TRADEMARK OFFICE
CERTIFICATE OF CORRECTION

PATENT NO. : 5,296,363
DATED : March 22, 1994
INVENTOR(S) : COOPER et al.

It is certified that error appears in the above-indentified patent and that said Letters Patent is hereby corrected as shown below:

On the title page, item [73], the assignee should read --BASF Akteingesellschaft--.

Claim 1, column 6, line 66, "acid of salts" should be --acid or salts--.

Signed and Sealed this

Twenty-third Day of August, 1994

Attest:

BRUCE LEHMAN

Attesting Officer

Commissioner of Patents and Trademarks